(12) United States Patent
Klemarczyk et al.

(10) Patent No.: US 8,524,034 B2
(45) Date of Patent: Sep. 3, 2013

(54) HYDROGEN PEROXIDE COMPLEXES AND THEIR USE IN THE CURE SYSTEM OF ANAEROBIC ADHESIVES

(75) Inventors: Philip T. Klemarczyk, Canton, CT (US); David Birkett, Naas (IE); David Farrell, Dublin (IE); Peter Wrobel, Dublin (IE); Ciaran McArdle, Dublin (IE); Greg Clarke, Blessington (IE)

(73) Assignees: Henkel Corporation, Rocky Hill, CT (US); Henkel Ireland Limited, Monheim (DE)

( * ) Notice: Subject to any disclaimer, the term of this patent is extended or adjusted under 35 U.S.C. 154(b) by 0 days.

(21) Appl. No.: 13/177,921

(22) Filed: Jul. 7, 2011

(65) Prior Publication Data
US 2011/0290418 A1 Dec. 1, 2011

Related U.S. Application Data

(63) Continuation of application No. PCT/US2010/020206, filed on Jan. 6, 2010.

(60) Provisional application No. 61/143,001, filed on Jan. 7, 2009.

(51) Int. Cl.
B32B 37/12 (2006.01)
C07C 233/31 (2006.01)
C07C 275/02 (2006.01)
C07D 207/26 (2006.01)

(52) U.S. Cl.
USPC ...... 156/332; 526/220; 526/204; 252/182.18; 252/182.23; 252/182.28; 564/32; 564/204; 548/543

(58) Field of Classification Search
USPC ............ 156/332; 526/220, 204; 252/182.18, 252/182.23, 182.28; 564/32, 204; 548/543
See application file for complete search history.

(56) References Cited

U.S. PATENT DOCUMENTS 3,218,305 A 11/1965 Krieble
4,180,640 A 12/1979 Melody et al.
(Continued)

FOREIGN PATENT DOCUMENTS
CN 1418871 5/2003
FR 1581361 9/1969

OTHER PUBLICATIONS
Lu, Hughes and Giguere, J. Am. Chem. Soc., 1941, v. 63 pp. 1507-1513.
(Continued)

*Primary Examiner* — Michael Orlando
*Assistant Examiner* — Daniel Lee
(74) *Attorney, Agent, or Firm* — Steven C. Bauman

(57) ABSTRACT

Provided is a complex of hydrogen peroxide and at least one compound represented by Formula I:

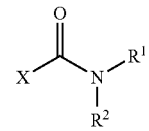

(I)

wherein X is:

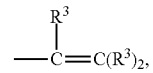

$-C(R^3)_3$, $-C\equiv C(R^3)$, $-O(R^3)$, $-N(R^3)_2$, or $-S(R^3)$; and $R^1$, $R^2$, and $R^3$ are each independently selected from H, alkyl, alkenyl, alkynyl, aralkyl, aryl, heteroaryl heteroarylalkyl, heterocyclyl, and cycloalkyl, or $R^2$ and an $R^3$ are optionally taken together to form an alicyclic ring. Also provided are anaerobic cure systems and curable compositions employing the complexes described herein.

19 Claims, 3 Drawing Sheets

(56) References Cited

U.S. PATENT DOCUMENTS

| | | | |
|---|---|---|---|
| 4,287,330 A | 9/1981 | Rich | |
| 4,321,349 A | 3/1982 | Rich | |
| 4,446,246 A * | 5/1984 | McGinniss | 502/155 |
| 4,855,001 A * | 8/1989 | Damico et al. | 156/307.3 |
| 5,206,385 A | 4/1993 | Login et al. | |
| 5,520,727 A | 5/1996 | Vreeland et al. | |
| 5,605,999 A | 2/1997 | Chu et al. | |
| 5,770,739 A * | 6/1998 | Lin et al. | 548/335.5 |
| 5,811,473 A * | 9/1998 | Ramos et al. | 523/176 |
| 6,391,993 B1 | 5/2002 | Attarwala et al. | |
| 6,583,289 B1 | 6/2003 | McArdle et al. | |
| 6,835,762 B1 * | 12/2004 | Kelmarczyk et al. | 523/176 |
| 6,835,782 B1 | 12/2004 | Morita et al. | |
| 6,958,368 B1 | 10/2005 | Klemarczyk et al. | |
| 7,411,005 B2 | 8/2008 | Ninkov | |
| 7,411,025 B1 | 8/2008 | Messana et al. | |
| 2005/0266095 A1 * | 12/2005 | Xia et al. | 424/616 |

OTHER PUBLICATIONS

International Search Report issued in connection with International Patent Application No. PCT/US2010/020206 mailed Aug. 17, 2010.

Supplementary European Search Report mailed Jun. 28, 2012.

* cited by examiner

HYDROGEN PEROXIDE COMPLEXES AND THEIR USE IN THE CURE SYSTEM OF ANAEROBIC ADHESIVES

BACKGROUND

1. Field

The present invention relates to hydrogen peroxide complexes as well as anaerobic curable compositions employing these complexes.

2. Brief Description of Related Technology

Anaerobic adhesive compositions are well known for their ability to remain in a liquid, unpolymerized state in the presence of oxygen and to cure to a solid state upon the exclusion of oxygen. Early work on anaerobic adhesive compositions concentrated on developing a cure system which improved the speed and/or bond strength of the adhesive composition. Various cure systems for anaerobic adhesive compositions have been developed to primarily focus on efficiently performing the redox reaction, which is the basis for anaerobic chemistry.

Anaerobic compositions generally contain (meth)acrylic functional monomers, an organic hydroperoxy or perester initiator, accelerators such as saccharin and/or dimethyl-p-toluidene, stabilizers such as hydroquinone or other phenolic stabilizers and metal chelators such as sodium EDTA. Those persons of ordinary skill in the art acknowledge that peroxides serve as a free radical generating source which initiate free radical curing of the polymerizable anaerobic adhesive monomer compositions. Illustrative of such initiators are the diacyl peroxides such as benzoyl peroxide; dialkyl peroxides such as di-tert-butyl peroxide; ketone peroxides such as methylethyl ketone peroxide; and peresters which readily hydrolyze, e.g., tert-butyl peracetate, tert-butyl perbenzoate and di-tert-butyl diperphthalate.

A particularly useful class of peroxy initiators is the organic hydroperoxides such as cumene hydroperoxide ("CHP"), methylethylketone hydroperoxide, tert-butyl hydroperoxide ("TBH") and methylethyl ketone hydroperoxide. Of these, cumene hydroperoxide is especially popular. However, the peroxy initiators currently used in the art suffer from several deficiencies. For instance, alkyl hydroperoxides, such as cumene hydroperoxide, have a distinctive, objectionable odor. In addition, there are concerns about the toxicity of cumene hydroperoxide.

Notwithstanding the state of the art, there is an on-going desire to find alternative technologies for peroxy initiators and anaerobic compositions to differentiate existing products, overcome deficiencies in the art and provide supply assurances in the event of shortages or cessation of supply of raw materials. Accordingly, it would be desirable to identify new materials that function as a peroxy initiator and can be used in anaerobically curable compositions.

SUMMARY

In some non-limiting embodiments, a complex is provided which comprises hydrogen peroxide and at least one compound represented by Formula I:

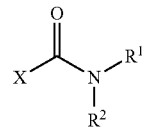

wherein X is:

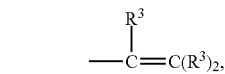

—$C(R^3)_3$, —$C\equiv C(R^3)$, —$O(R^3)$, —$N(R^3)_2$, or —$S(R^3)$; and $R^1$, $R^2$ and $R^3$ are each independently selected from H, alkyl, alkenyl, alkynyl, aralkyl, aryl, heteroaryl heteroarylalkyl, heterocyclyl, and cycloalkyl, or $R^2$ and an $R^3$ are optionally taken together to form an alicyclic ring.

In some non-limiting embodiments, an anaerobic curable composition is provided which comprises: (a) a complex of hydrogen peroxide and at least one compound represented by Formula I:

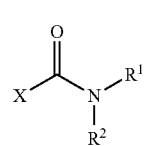

wherein X is:

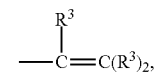

—$C(R^3)_3$, —$C\equiv C(R^3)$, —$O(R^3)$, —$N(R^3)_2$, or —$S(R^3)$; and $R^1$, $R^2$ and $R^3$ are each independently selected from H, alkyl, alkenyl, alkynyl, aralkyl, aryl, heteroaryl heteroarylalkyl, heterocyclyl, and cycloalkyl, or $R^2$ and an $R^3$ are optionally taken together to form an alicyclic ring; and (b) a (meth)acrylate component.

In some non-limiting embodiments, a method of preparing an anaerobic curable composition is provided which comprises the step of mixing together a meth(acrylate) component and an anaerobic cure system which comprises a complex of hydrogen peroxide and at least one compound represented by Formula I:

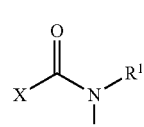

wherein X is:

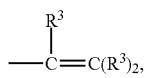

—C(R³)₃, —C≡C(R³), —O(R³), —N(R³)₂, or —S(R³); and R¹, R² and R³ are each independently selected from H, alkyl, alkenyl, alkynyl, aralkyl, aryl, heteroaryl heteroarylalkyl, heterocyclyl, and cycloalkyl, or R² and an R³ are optionally taken together to form an alicyclic ring.

In some non-limiting embodiments, a method of bonding two or more substrates is provided which comprises the steps of: (a) providing at least two substrates; (b) dispensing onto a surface of one or both of the at least two substrates an adhesive composition comprising: (1) a complex comprising hydrogen peroxide and at least one compound represented by Formula I:

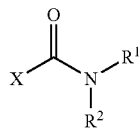

wherein X is:

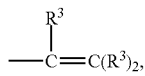

—C(R³)₃, —C≡C(R³), —O(R³), —N(R³)₂, or —S(R³); and R¹, R² and R³ are each independently selected from H, alkyl, alkenyl, alkynyl, aralkyl, aryl, heteroaryl heteroarylalkyl, heterocyclyl, and cycloalkyl, or R² and an R³ are optionally taken together to form an alicyclic ring; and (2) a (meth)acrylate component; (c) contacting the surfaces of the at least two substrates having the adhesive composition thereon; and (d) exposing the adhesive composition to curing conditions.

BRIEF DESCRIPTION OF THE DRAWINGS

The foregoing summary, as well as the following detailed description, will be better understood when read in conjunction with the appended drawings. In the drawings.

DETAILED DESCRIPTION

Figure 1:
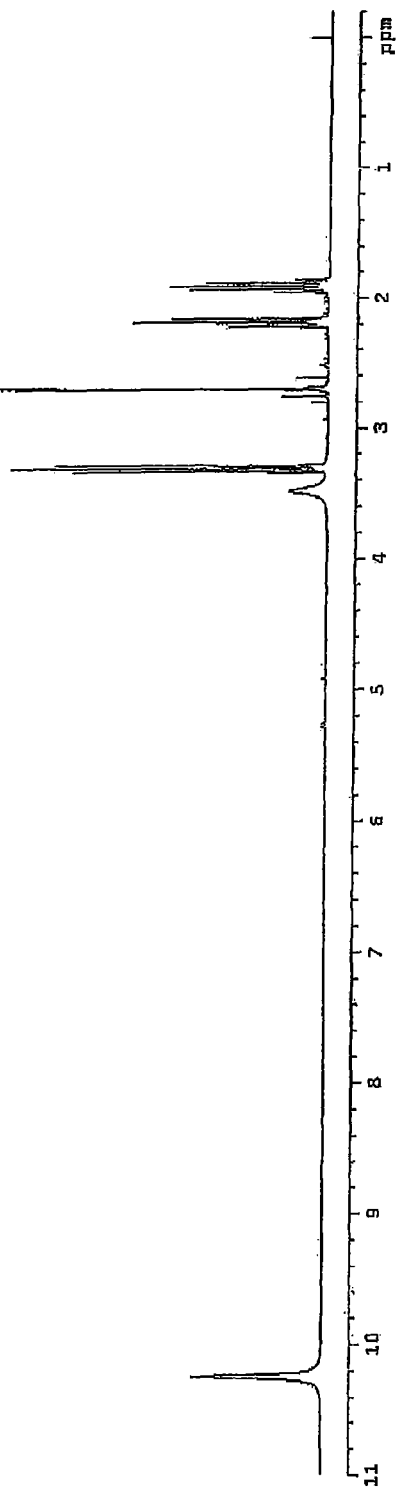
FIG. 1 depicts an ¹H NMR spectrum of a N-methyl pyrrolidinone+H₂O₂ complex of Example 3 according to the present invention.

Other than in the operating examples, or where otherwise indicated, all numbers expressing quantities of ingredients, thermal conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements. Furthermore, when numerical ranges of varying scope are set forth herein, it is contemplated that any combination of these values inclusive of the recited values may be used.

Also, it should be understood that any numerical range recited herein is intended to include all sub-ranges subsumed therein. For example, a range of "1 to 10" is intended to include all sub-ranges between and including the recited minimum value of 1 and the recited maximum value of 10, that is, having a minimum value equal to or greater than 1 and a maximum value of equal to or less than 10.

As used herein, the term "composition" is intended to encompass a product comprising the specified ingredients in the specified amounts, as well as any product which results, directly or indirectly, from combination of the specified ingredients in the specified amounts.

As used herein, the term "cured" as used in connection with a composition, e.g., "composition when cured" or a "cured composition", means that any curable or crosslinkable components of the composition are at least partially cured or crosslinked. In some non-limiting embodiments, the chemical conversion of the crosslinkable components, i.e., the degree of crosslinking, ranges from about 5% to about 100% of complete crosslinking where complete crosslinking means full reaction of all crosslinkable components. In other non-limiting embodiments, the degree of crosslinking ranges from about 15% to about 80% or about 50% to about 60% of full crosslinking. One skilled in the art will understand that the presence and degree of crosslinking, i.e., the crosslink density, can be determined by a variety of methods, such as dynamic mechanical thermal analysis (DMA) using a TA Instruments DMA 2980 DMA analyzer over a temperature range of −65° F. (−18° C.) to 350° F. (177° C.) conducted under nitrogen according to ASTM D 4065-01. This method determines the glass transition temperature and crosslink density of free films of coatings or polymers. These physical properties of a cured material are related to the structure of the crosslinked network.

As used herein, "equivalents" means molar equivalents unless otherwise indicated. With respect to a complex, the number of equivalents is equal to the number of moles of the complex formed.

Figure 3:
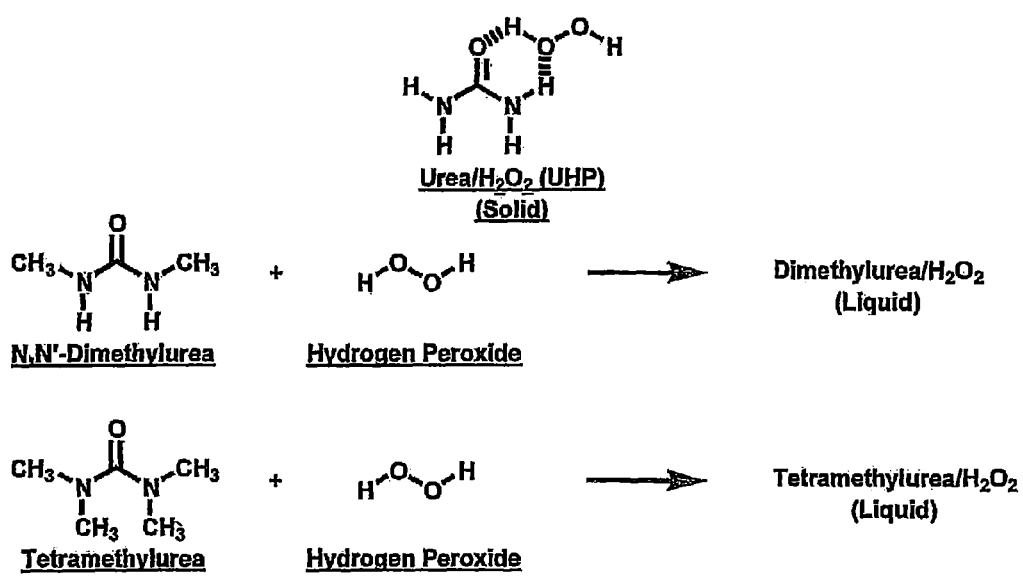
FIG. 3 depicts a representative structure of a urea+H₂O₂ complex as well as synthetic schemes to arrive at a N,N' dimethylurea+H₂O₂ complex and a tetramethylurea+H₂O₂ complex.

The term "complex" refers to a molecular entity formed by the association of two or more molecules, usually by non-covalent bonding, such as hydrogen or ionic bonding. With respect to a complex of hydrogen peroxide and one or more organic compounds, formation of the complex is commonly attributed to hydrogen bonding between electron-rich functional groups in the organic compound and the peroxide hydrogen. For illustrative purposes only, FIG. 3 depicts a representative structure of a complex of urea and hydrogen peroxide where the dashed bond lines represent the associative forces between the molecules formed from, i.e., hydrogen bonding.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent. The phrase "optionally substituted" means optional substitution with the specified groups, radicals, or moieties.

The term "interrupted" means that a designated atom along the backbone of the compound is replaced with a selection from the indicated group, provided that the designated atom's normal valency under the existing circumstances is not exceeded, and that the interruption results in a stable compound. By "stable compound" or "stable structure" is meant a compound that is sufficiently robust to survive isolation to a useful degree of purity from a reaction mixture, and formulation into an efficacious therapeutic agent. The phrase "optionally interrupted" means optional interruption of the backbone with the specified groups, radicals or moieties.

As used herein, "formed from" or "prepared from" denotes open, e.g., "comprising," claim language. As such, it is intended that a composition "formed from" or "prepared from" a list of recited components be a composition comprising at least these recited components or the reaction product of at least these recited components, and can further comprise other, non-recited components, during the composition's formation or preparation.

The invention concerns hydrogen peroxide complexes and anaerobic curable compositions employing these complexes which can be useful in polymerizable (curable) adhesives and sealants. Anaerobic compositions are commonly composed of curable unsaturated monomers, specifically methacrylate ester monomers, in combination with an anaerobic cure system, which may include one or more peroxy-based polymerization initiators.

The present inventors have discovered hydrogen peroxide complexes that can be used as the peroxy-based polymerization initiators in the cure system of anaerobic curable compositions, and particularly anaerobic adhesives. The addition of these complexes as a replacement for some or all of the conventional peroxy-based initiators which include alkyl hydroperoxide initiators (such as cumene hydroperoxide) surprisingly provides at least comparable cure speeds and physical properties for the products formed therefrom, as compared with those observed from conventional anaerobic curable compositions. As such, these materials provide many benefits to anaerobic adhesives, including but not limited to: reduced odor and safety concerns, reduced bioavailability, good formulation stability, and good solubility in anaerobic curable compositions.

In some non-limiting embodiments, the present invention provides a complex comprising hydrogen peroxide and at least one compound represented by Formula I:

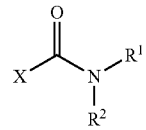

wherein X is:

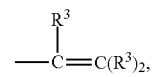

—C(R$^3$)$_3$, —C≡C(R$^3$), —O(R$^3$), —N(R$^3$)$_2$, or —S(R$^3$); and R$^1$, R$^2$ and R$^3$ are each independently selected from H, alkyl, alkenyl, alkynyl, aralkyl, aryl, heteroaryl heteroarylalkyl, heterocyclyl, and cycloalkyl, or R$^2$ and an R$^3$ are optionally taken together to form an alicyclic ring.

"Alkyl" means an aliphatic hydrocarbon group which may be straight or branched and comprising about 1 to about 20 carbon atoms in the chain, about 1 to about 12 carbon atoms in the chain, or about 1 to about 6 carbon atoms in the chain. Branched means that one or more lower alkyl groups such as methyl, ethyl, or propyl, are attached to a linear alkyl chain. "Lower alkyl" means a group having about 1 to about 6 carbon atoms in the chain which may be straight or branched. The alkyl group may be unsubstituted or optionally substituted by one or more substituents which may be the same or different, each substituent being independently selected from halo, alkyl, aryl, cycloalkyl, cyano, hydroxy, alkoxy, alkylthio, amino, —NH(alkyl), —NH(cycloalkyl), —N(alkyl)$_2$, carboxy, and —C(O)O-alkyl. The alkyl group may be optionally interrupted by atoms or groups independently selected from oxygen, sulfur, phenylene, sulphinyl, sulphonyl, carbonyl, N—R$_b$, or C=O—OR$_b$ wherein R$_b$ can be hydrogen, alkyl, cycloalkyl, alkenyl, cycloalkenyl, alkynyl, aryl, acyl, or aralkyl. Non-limiting examples of suitable alkyl groups include methyl, ethyl, n-propyl, isopropyl, t-butyl, and diacetone.

"Alkenyl" means a monovalent, unbranched, or branched hydrocarbon chain having one or more double bonds therein. The double bond of an alkenyl group can be unconjugated or conjugated to another unsaturated group. Suitable alkenyl groups include, but are not limited to (C$_2$-C$_8$) alkenyl groups, such as vinyl, allyl, butenyl, pentenyl, hexenyl, butadienyl, pentadienyl, hexadienyl, 2-ethylhexenyl,2-propyl-2-butenyl, 4-(2-methyl-3-butene)-pentenyl. An alkenyl group can be unsubstituted or substituted with one or two suitable substituents. The alkenyl group may be optionally interrupted by atoms or groups independently selected from oxygen, sulfur, phenylene, sulphinyl, sulphonyl, carbonyl, N—R$_b$, or C=O—OR$_b$ wherein R$_b$ can be hydrogen, alkyl, cycloalkyl, alkenyl, cycloalkenyl, alkynyl, aryl, acyl, or aralkyl.

"Alkynyl" means a monovalent, unbranched or branched hydrocarbon chain having one or more triple bonds therein. The triple bond of an alkynyl group can be unconjugated or conjugated to another unsaturated group. Suitable alkynyl groups include, but are not limited to, (C$_2$-C$_8$) alkynyl groups, such as ethynyl, propynyl, butynyl, pentynyl, hexynyl, methylpropynyl, 4-methyl-1-butynyl,4-propyl-2-pentynyl-, and 4-butyl-2-hexynyl. An alkynyl group can be unsubstituted or substituted with one or two suitable substituents. The alkynyl group may be optionally interrupted by atoms or groups independently selected from oxygen, sulfur, phenylene, sulphinyl, sulphonyl, carbonyl, N—$R_b$, or C=O—$OR_b$ wherein $R_b$ can be hydrogen, alkyl, cycloalkyl, alkenyl, cycloalkenyl, alkynyl, aryl, acyl, or aralkyl.

"Aralkyl" means a radical in which an aryl group, as defined below, is substituted for a hydrogen atom of an alkyl group, as defined above.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example, nitrogen, oxygen or sulfur, alone or in combination. Non-limiting examples of useful heteroaryls include those containing about 5 to about 6 ring atoms. The "heteroaryl" can be optionally substituted by one or more "ring system substituents" which may be the same or different, and are as defined herein. The prefix aza, oxa, or thia before the heteroaryl root name means that at least one of a nitrogen, oxygen, or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl, and the like. The term "heteroaryl" also refers to partially saturated heteroaryl moieties such as, for example, tetrahydroisoquinolyl, tetrahydroquinolyl, and the like.

"Heteroarylalkyl" means a radical of the formula —$R_aR_f$— where $R_a$ is an alkyl as defined above and $R_f$ is a heteroaryl radical as defined above. The heteroaryl part of the heteroarylalkyl radical may be optionally substituted as defined above for a heteroaryl group. The alkyl part of the heteroarylalkyl radical may be optionally substituted as defined above for an alkyl group.

"Cycloalkyl" means an unsaturated or saturated hydrocarbon that forms at least one ring, having from 3 to 20 ring carbon atoms, preferably from 3 to 10 ring carbon atoms. The rings in a cycloalkyl group are not aromatic. A cycloalkyl group can be unsubstituted or substituted and includes cycloalkenyl groups.

"Heterocyclyl" means a 4-7 membered non-aromatic cyclic group containing one, two or three heteroatom(s) independently selected from N, O, and S. The heterocyclyl group can be optionally substituted with one or more "ring system substituents" which may be the same or different, and are as defined herein. Examples include pyrrolidinyl, imidazolidinyl, pyrazolidinyl, isothiazolyl, thiazolyl, piperidinyl, piperazinyl, morpholinyl, thiomorpholinyl, tetrahydrofuranyl, dioxolanyl, tetrahydrothienyl, dioxanyl, and dithianyl.

"Alicyclic" means a group that is both aliphatic and cyclic and contains one or more carbon rings which may be either saturated or unsaturated but not aromatic. The heterocyclyl group can be optionally substituted with one or more "ring system substituents" which may be the same or different, and are as defined herein. Non-limiting examples of alicyclic rings include cycloalkanes, such as cyclopropane, cyclobutane, and cyclohexane, polycyclic cycloalkanes, and bicyclic alkanes, such as norbornene and norbornadiene.

"Ring system substituent" means a substituent attached to an aromatic or non-aromatic ring system which, for example, replaces an available hydrogen on the ring system. Ring system substituents may be the same or different, each being independently selected from the alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —C(=N—CN)—$NH_2$, —C(=NH)—$NH_2$, —C(=NH)—NH(alkyl), $Y_1Y_2N$—, $Y_1Y_2$N-alkyl-, $Y_1Y_2NC(O)$—, $Y_1Y_2NSO_2$— and —$SO_2NY_1Y_2$, wherein $Y_1$ and $Y_2$ can be the same or different and are independently selected from hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system.

In some non-limiting embodiments, the compound of Formula I may be a urea compound according to Formula II:

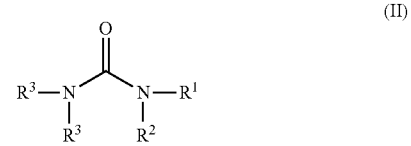

wherein in Formula II: $R^1$, $R^2$, and each $R^3$ are each independently selected from H, alkyl, alkenyl, alkynyl, aralkyl, aryl, heteroaryl heteroarylalkyl, heterocyclyl, and cycloalkyl. In some non-limiting embodiments, $R^2$ and one $R^3$ can be optionally taken together to form an alicyclic ring. In some preferred embodiments, each of $R^1$, $R^2$, and each $R^3$ are independently selected from H and lower ($C_1$-$C_6$) alkyl, such as $C_1$-$C_3$ alkyl.

Non-limiting examples of compounds of Formula II include:

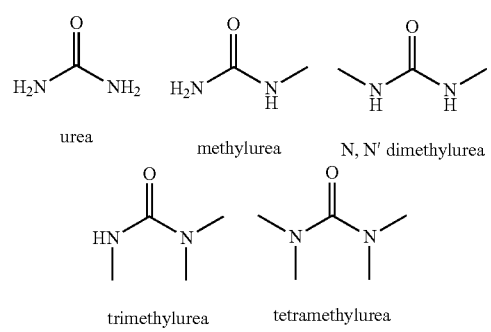

In some non-limiting embodiments, the compound of Formula I may be an acrylic amide compound according to Formula III:

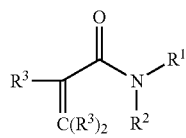

(III)

wherein in Formula III: $R^1$, $R^2$ and $R^3$ are each independently selected from H, alkyl, alkenyl, alkynyl, aralkyl, aryl, heteroaryl heteroarylalkyl, heterocyclyl, and cycloalkyl.

Non-limiting examples of compounds of Formula III include:

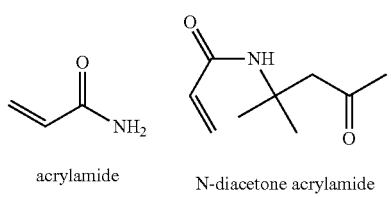

acrylamide    N-diacetone acrylamide

In some non-limiting embodiments, the compound of Formula I may be a pyrrolidinone compound according to Formula IV:

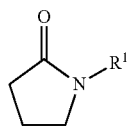

(IV)

wherein in Formula IV: $R^1$ is selected from H, alkyl, alkenyl, alkynyl, aralkyl, aryl, heteroaryl heteroarylalkyl, heterocyclyl, and cycloalkyl. In some non-limiting embodiments, $R^1$ is alkyl, such as $C_1$-$C_{12}$ alkyl.

Non-limiting examples of compounds of Formula IV include:

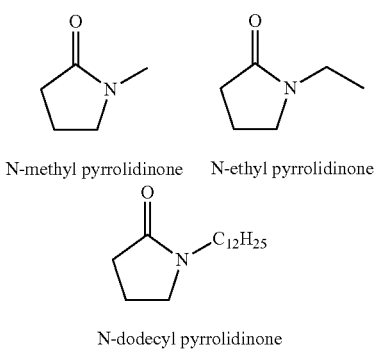

N-methyl pyrrolidinone    N-ethyl pyrrolidinone

N-dodecyl pyrrolidinone

The complexes of the present invention may be prepared using conventional methods which are well known to those persons of skill in the art. Common methods of producing complexes include crystallization of the complex from an aqueous solution by adding the complexing compound (here, the compound of Formula I) to a solution of hydrogen peroxide and allowing the complex to crystallize under the proper conditions. See, e.g., Lu, Hughes and Giguere (J. Am. Chem. Soc., 1941, v. 63 pgs. 1507-1513). Non-aqueous methods of preparing a hydrogen peroxide complex are also known, as described in U.S. Pat. No. 5,770,739 (Lin).

In some non-limiting embodiments, the hydrogen peroxide is present in an amount ranging from about 0.33 to about 2.0 equivalents based on the total equivalents of the complex, such as from about 0.66 to about 1.5.

The complexes of the present invention can be combined with one or more anaerobic cure components, such as accelerators, stabilizers, and reducing agents, to form an anaerobic cure system.

Non-limiting examples of useful cure components include:
(i) arylamines of the formula:

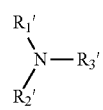

in which $R_1'$ is an optionally substituted aryl radical, more especially an optionally alkyl-substituted phenyl radical, $R_2'$ has the same meaning as $R_1'$ or is an optionally substituted, linear or branched alkyl radical and $R_3'$ is a linear or branched alkyl radical which may be substituted, but contains at least one hydrogen atom in the alpha-position to the nitrogen and any two of $R_1'$, to $R_3'$, may together form a mono- or polycyclic ring structure, which may optionally be a fused ring structure, and which in turn may be substituted;
(ii) a compound having the formula:

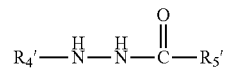

wherein $R_4'$ is phenyl substituted with $C_1$-$C_4$ alkyl group and $R_5'$ is selected from hydrogen, alkyl, cycloalkyl, alkenyl, cycloalkenyl, aryl, alkoxy, aryloxy, carbonyl, amino and the following groups:

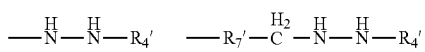

wherein $R_7'$ is selected from alkyl groups containing one to about 10 carbon atoms;
(iii) sulphonyl hydrazines; or
(iv) hydropyridines.

Specific non-limiting examples include saccharin, toluidines, such as N,N-diethyl-p-toluidine ("DE-p-T") and N,N-dimethyl-o-toluidine ("DM-o-T"), acetyl phenylhydrazine ("APH"), and maleic acid. See e.g. U.S. Pat. Nos. 3,218,305 (Krieble), 4,180,640 (Melody), 4,287,330 (Rich) and 4,321,349 (Rich). Additional useful accelerators include sulfinimides and oxygen and sulfur derivatives thereof such as described in U.S. Pat. No. 6,958,368 (Klemarczyk); phenylglycines and derivatives thereof, 1,4-aminobenzoyl compounds, and phenyl pyrazolinones such as disclosed in U.S. Pat. No. 7,411,025 (Messana); sulfonimide derivatives and sulfonamide derivatives as disclosed in U.S. Pat. No. 7,411,005 (Messana); trithiadiaza pentalenes as described in U.S. Pat. No. 6,583,289 (McCardle); the reaction product of succinic anhydride and phenyl hydrazine ("SPH"), which can be prepared according to U.S. Pat. No. 6,835,782 (Morita); and compounds including the —C(═O)—NH—NH— linkage together with an organic acid functional group on the same molecule, as disclosed in U.S. Pat. No. 6,835,762 (Klemarczyk).

The anaerobic cure systems of the present invention may be prepared using conventional methods which are well known to those persons of skill in the art. For instance, the components of the cure system may be mixed together in any convenient order consistent with the roles and functions the components are to perform in the cure system. Conventional mixing techniques using known apparatus may be employed.

In some non-limiting embodiments, the present invention provides an anaerobic curable composition. Generally, anaerobic curable compositions are based on a (meth)acrylate component together with an anaerobic cure-inducing composition. In some non-limiting embodiments, the anaerobic curable composition of the present invention is based on the (meth)acrylate component, together with the anaerobic cure system described above.

(Meth)acrylate monomers suitable for use as the (meth) acrylate component in the anaerobic curable compositions of the present invention may be selected from a wide variety of materials, such as those represented by $H_2C=CGCO_2R^8$, where G may be hydrogen, halogen or alkyl groups having from 1 to about 4 carbon atoms, and $R^8$ may be selected from alkyl, cycloalkyl, alkenyl, cycloalkenyl, alkaryl, aralkyl, or aryl groups having from 1 to about 16 carbon atoms, any of which may be optionally substituted or interrupted as the case may be with silane, silicon, oxygen, halogen, carbonyl, hydroxyl, ester, carboxylic acid, urea, urethane, carbonate, amine, amide, sulfur, sulfonate, sulfone, and the like.

Additional (meth)acrylate monomers suitable for use herein include polyfunctional (meth)acrylate monomers, for example, di- or tri-functional (meth)acrylates such as polyethylene glycol di(meth)acrylates, tetrahydrofuran (meth) acrylates and di(meth)acrylates, hydroxypropyl (meth)acrylate ("HPMA"), hexanediol di(meth)acrylate, trimethylol propane tri(meth)acrylates ("TMPTMA"), diethylene glycol dimethacrylate, triethylene glycol dimethacrylates ("TRIEGMA"), tetraethylene glycol di(meth)acrylates, dipropylene glycol di(meth)acrylates, di-(pentamethylene glycol) di(meth)acrylates, tetraethylene diglycol di(meth)acrylates, diglycerol tetra(meth)acrylates, tetramethylene di(meth) acrylates, ethylene di(meth)acrylates, neopentyl glycol di(meth)acrylates, and bisphenol-A mono and di(meth)acrylates, such as ethoxylated bisphenol-A (meth)acrylate ("EBIPMA"), and bisphenol-F mono and di(meth)acrylates, such as ethoxylated bisphenol-A (meth)acrylate.

Still other (meth)acrylate monomers that may be used herein include silicone (meth)acrylate moieties ("SiMA"), such as those taught by and claimed in U.S. Pat. No. 5,605,999 (Chu), incorporated herein by reference.

Other suitable monomers include polyacrylate esters represented by the formula

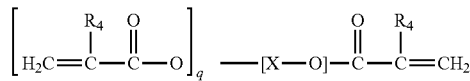

wherein $R^4$ is a radical selected from hydrogen, halogen, and alkyl of from 1 to about 4 carbon atoms; q is an integer equal to at least 1, and preferably equal to from 1 to about 4; and X is an organic radical containing at least two carbon atoms and having a total bonding capacity of q plus 1. With regard to the upper limit for the number of carbon atoms in X, workable monomers exist at essentially any value. As a practical matter, however, a general upper limit is about 50 carbon atoms, preferably 30, and most preferably about 20.

For example, X can be an organic radical of the formula:

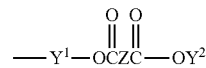

wherein each of $Y^1$ and $Y^2$ is an organic radical, preferably a hydrocarbon group, containing at least 2 carbon atoms, and preferably from 2 to about 10 carbon atoms, and Z is an organic radical, preferably a hydrocarbon group, containing at least 1 carbon atom, and preferably from 2 to about 10 carbon atoms.

Other classes of useful monomers are the reaction products of di- or tri-alkylolamines (e.g., ethanolamines or propanolamines) with acrylic acids, such as are disclosed in French Patent No. 1,581,361.

Non-limiting examples of useful acrylic ester oligomers include those having the following general formula:

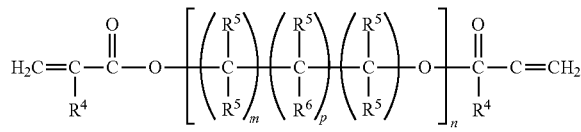

wherein $R^5$ represents a radical selected from hydrogen, lower alkyl of from 1 to about 4 carbon atoms, hydroxy alkyl of from 1 to about 4 carbon atoms, and

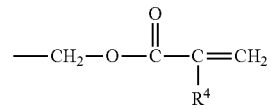

wherein $R^4$ is a radical selected from hydrogen, halogen, and lower alkyl of from 1 to about 4 carbon atoms; $R^6$ is a radical selected from hydrogen, hydroxyl, and

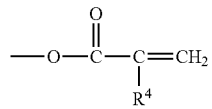

m is an integer equal to at least 1, e.g., from 1 to about 15 or higher, and preferably from 1 to about 8; n is an integer equal to at least 1, e.g., 1 to about 40 or more, and preferably between about 2 and about 10; and p is 0 or 1.

Typical examples of acrylic ester oligomers corresponding to the above general formula include di-, tri- and tetraethyleneglycol dimethacrylate; di(pentamethyleneglycol) dimethacrylate; tetraethyleneglycol diacrylate; tetraethyleneglycol di(chloroacrylate); diglycerol diacrylate; diglycerol tetramethacrylate; butyleneglycol dimethacrylate; neopentylglycol diacrylate; and trimethylolpropane triacrylate.

While di- and other polyacrylate esters, and particularly the polyacrylate esters described in the preceding paragraphs, can be desirable, monofunctional acrylate esters (esters containing one acrylate group) also may be used. When dealing with monofunctional acrylate esters, it is highly preferable to use an ester which has a relatively polar alcoholic moiety. Such materials are less volatile than low molecular weight alkyl esters and, more important, the polar group tends to provide intermolecular attraction during and after cure, thus producing more desirable cure properties, as well as a more durable sealant or adhesive. Most preferably, the polar group is selected from labile hydrogen, heterocyclic ring, hydroxy, amino, cyano, and halo polar groups. Typical examples of compounds within this category are cyclohexyl methacrylate, tetrahydrofurfuryl methacrylate, hydroxyethyl acrylate, hydroxypropyl methacrylate ("HPMA"), t-butylaminoethyl methacrylate, cyanoethylacrylate, and chloroethyl methacrylate.

Another useful class of monomers is prepared by the reaction of a monofunctionally substituted alkyl or aryl acrylate ester containing an active hydrogen atom on the functional substituent. This monofunctional, acrylate-terminated material is reacted with an organic polyisocyanate in suitable proportions so as to convert all of the isocyanate groups to urethane or ureido groups. The monofunctional alkyl and aryl acrylate esters are preferably the acrylates and methacrylates containing hydroxy or amino functional groups on the nonacrylate portion thereof. Acrylate esters suitable for use have the formula

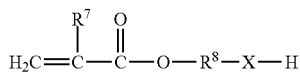

wherein X is selected from —O— and

and $R^9$ is selected from hydrogen and lower alkyl of 1 through 7 carbon atoms; $R^7$ is selected from hydrogen, chlorine and methyl and ethyl radicals; and $R^8$ is a divalent organic radical selected from lower alkylene of 1 through 8 carbon atoms, phenylene or naphthylene. These groups upon proper reaction with a polyisocyanate, yield:

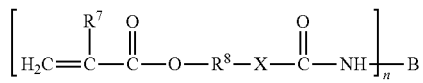

wherein n is an integer from 2 to about 6; B is a polyvalent organic radical selected from alkyl, alkenyl, cycloalkyl, cycloalkenyl, aryl, aralkyl, alkaryl or heterocyclic radicals both substituted and unsubstituted; and $R^7$, $R^8$ and X have the meanings given above.

The hydroxy- and amine-containing materials suitable for use in the preparation of the above monomeric products are exemplified by, but not limited to, such materials as hydroxyethyl acrylate, hydroxyethyl methacrylate, aminoethyl methacrylate, 3-hydroxypropyl methacrylate, aminopropyl methacrylate, hydroxyhexyl acrylate, t-butylaminoethyl methacrylate, and hydroxyoctyl methacrylate.

The preferred organic polyisocyanates comprise the higher alkenyl diisocyanates, the cycloalkenyl diisocyanates and the aromatic diisocyanates containing 8 or more carbon atoms and preferably from 8 to about 30 carbon atoms, such as, for example, octamethylene diisocyanate, durene diisocyanate, 4,4'-diphenyldiisocyanate, and toluene diisocyanate.

Of course, combinations of these (meth)acrylate monomers and other classes of monomers may also be used.

In curable compositions of the present invention, the complex of hydrogen peroxide and the one or more compounds of Formula I is typically employed in the range of from about 0.1 to about 10 percent by weight, based on the total weight of the composition, with about 1 to about 5 percent by weight being desirable.

In the curable compositions of the present invention, the (meth)acrylate component typically comprises from about 10 to about 90 percent by weight of the composition, such as about 60 to about 90 percent by weight, based on the total weight of the composition.

Recently, additional components have been included in traditional anaerobic curable compositions to alter the physical properties of either the curable compositions or the reaction products thereof. While these components are described in terms of additions to the anaerobic curable compositions, they may also be considered to be part of the anaerobic cure system described herein, as would be understood by one skilled in the art.

For instance, one or more of maleimide components, thermal resistance-conferring coreactants, diluent components reactive at elevated temperature conditions, mono- or poly-hydroxyalkanes, polymeric plasticizers, and chelators (see U.S. Pat. No. 6,391,993, the disclosure of which is hereby expressly incorporated herein by reference) may be included to modify the physical property and/or cure profile of the formulation and/or the strength or temperature resistance of the cured adhesive.

When used, the maleimide, coreactant, reactive diluent, plasticizer, and/or mono- or poly-hydroxyalkanes, may be present in an amount within the range of about 1 percent to about 30 percent by weight, based on the total weight of the anaerobic curable composition.

Stabilizers and inhibitors (such as phenols including hydroquinones and tetrahydroquinones and quinones, such as napthaquinone and anthraquinone) may also be employed to control and prevent premature peroxide decomposition and polymerization of the composition of the present invention, as well as chelating agents (such as the tetrasodium salt of ethylenediamine tetraacetic acid ("EDTA") and beta keto esters) to trap trace amounts of metal contaminants therefrom. When used, chelators may ordinarily be present in the compositions in an amount from about 0.001 percent by weight to about 0.1 percent by weight, based on the total weight of the anaerobic curable composition.

Metal catalyst solutions or pre-mixes thereof are used in amounts of about 0.03 to about 0.1 percent by weight. Other agents such as thickeners, non-reactive plasticizers, fillers, toughening components (such as elastomers and rubbers), and other well-known additives may be incorporated therein where the art-skilled believes it would be desirable to do so.

The present invention also provides methods of preparing and using the inventive anaerobic curable compositions.

The compositions of the present invention may be prepared using conventional methods which are well known to those persons of skill in the art. For instance, the components of the inventive compositions may be mixed together in any convenient order consistent with the roles and functions the components are to perform in the compositions. Conventional mixing techniques using known apparatus may be employed.

The compositions of this invention may be applied to a variety of substrates to perform with the desired benefits and advantages described herein. For instance, appropriate substrates may be constructed from steel, brass, copper, aluminum, zinc, glass and other metals and alloys, ceramics and thermosets. An appropriate primer may be applied to a surface of the chosen substrate to enhance cure rate. See e.g. U.S. Pat. No. 5,811,473 (Ramos). One particularly desirable use of the compositions disclosed herein is as a threadlocker, i.e., to secure a nut to a bolt. This is achieved by applying the composition to the threads of a bolt, mating it with a nut and allowing it to cure.

Curing can be accomplished over a wide range of times depending on specific composition, application and application geometry, curing temperature. For anaerobic compositions the cure speed typically varies from minutes (very fast) to days (very slow).

Curing of a polymerizable composition can be obtained by subjecting the composition to curing conditions, such as but not limited to heating, etc., leading to the reaction of reactive groups of the composition and resulting in polymerization and formation of a solid polymerizate. When a polymerizable composition is subjected to curing conditions, following polymerization and after reaction of most of the reactive groups occurs, the rate of reaction of the remaining unreacted reactive groups becomes progressively slower. In some non-limiting embodiments, the polymerizable composition can be subjected to curing conditions until it is at least partially cured. The term "at least partially cured" means subjecting the polymerizable composition to curing conditions, wherein reaction of at least a portion of the reactive groups of the composition occurs, to form a solid polymerizate. In some non-limiting embodiments, the polymerizable composition can be subjected to curing conditions such that a substantially complete cure is attained and wherein further exposure to curing conditions results in no significant further improvement in polymer properties, such as strength or hardness.

In addition, this invention provides a method of preparing an anaerobic curable composition, a step of which includes mixing together a (meth)acrylate component and an anaerobic cure system described above.

The invention also provides for an article prepared from the anaerobic curable compositions described herein.

The invention also provides a method of bonding two or more substrates using the anaerobic adhesive compositions of the present invention, the steps of which include applying the composition to a desired substrate surface and exposing the composition to an anaerobic environment for a time sufficient to cure the composition.

In view of the above description of the present invention, it is clear that a wide range of practical opportunities is provided. The following examples are provided for illustrative purposes only, and are not to be construed so as to limit in any way the teaching herein.

EXAMPLES

Example 1

An investigation was performed to evaluate urea-hydrogen peroxide complexes as potential replacements for alkyl hydroperoxides, and particularly cumene hydroperoxide, in anaerobic curable compositions.

Initial studies of model systems containing a urea hydrogen peroxide complex ("UHP"), Acetyl phenylhydrazine ("APH"), and triethylene glycol dimethacrylate ("TRIEGMA") showed similar bulk polymerization times when compared with analogous systems of cumene hydroperoxide ("CHP"), APH, and TRIEGMA.

A direct comparison of the suitability of UHP as a replacement for CHP in an anaerobic cure system was conducted by formulating the compositions of Table 1. UHP was easy to formulate and dissolved in the monomers easily. Moreover, UHP was essentially odorless.

TABLE 1

| Compound | Comparative Ex. (wt %) | Composition 1-1 (wt %) | Composition 1-2 (wt %) |
| --- | --- | --- | --- |
| hydroxypropyl (meth)acrylate ("HPMA") | 8.00 | 8.00 | 8.00 |
| isobornyl methacrylate ("IBOMA") | 15.00 | 15.00 | 15.00 |
| Phenoxyethyl Methacrylate | 27.14 | 27.69 | 27.14 |
| Urethane Methacrylate Resin | 24.34 | 24.34 | 24.34 |
| Radical Stabilizer | 0.25 | 0.25 | 0.25 |
| EDTA Chelator | 0.65 | 0.65 | 0.65 |
| Chelator Stabilizer | 0.65 | 0.65 | 0.65 |
| Saccharin | 0.75 | 0.75 | 0.75 |
| Acetyl phenylhydrazine ("APH") | 0.77 | 0.77 | 0.77 |
| Acrylic Acid | 1.00 | 1.00 | 1.00 |
| Phosphate Methacrylate | 0.10 | 0.10 | 0.10 |
| Methacryloxy ethyl succinate | 1.00 | 1.00 | 1.00 |
| Polyethylene particles | 6.50 | 6.50 | 6.50 |
| PTFE particles | 2.50 | 2.50 | 2.50 |
| Fluorescing Agent | 1.00 | 1.00 | 1.00 |
| Pigment | 0.02 | 0.02 | 0.02 |
| Cumene Hydroperoxide ("CHP") | 1.50 | 0 | 0 |
| Urea hydrogen peroxide complex ("UHP") | 0 | 0.95 | 1.50 |
| Fumed Silica | 8.83 | 8.83 | 8.83 |
| Total | 100.00 | 100.00 | 100.00 |

Bond strength tests were carried out according to testing method ASTM D1002-05. In addition, the 82° C. stability of the formulations was determined according to an evaluation in which the formulation is judged to have acceptable shelf stability if the adhesive formulation remains liquid for 3 hours or longer at 82° C. The results are shown in Table 2 below. Poorer 82° C. stability was seen particularly at the higher level of UHP (Composition 1-2). Composition 1-2 did, however, set up after a few days.

TABLE 2

| Test | Comparative Ex. | Composition 1-1 | Composition 1-2 |
| --- | --- | --- | --- |
| 24 hr. room temp. cure on SWAI at 0 gap | 9.1 N/mm$^2$ | 3.4 N/mm$^2$ | 4.6 N/mm$^2$ |
| 24 hr. room temp. cure on SWAI at 0.125 mm gap | 4.2 N/mm$^2$ | 0.8 N/mm$^2$ | 1.4 N/mm$^2$ |
| 24 hr. room temp. cure on GBMS at 0 gap | 9.05 N/mm$^2$ | 9.2 N/mm$^2$ | 6.2 N/mm$^2$ |
| 24 hr. room temp. cure on GBMS at 0.125 mm gap | 6.6 N/mm$^2$ | 2.2 N/mm$^2$ | 1.6 N/mm$^2$ |
| 82° C. stability | >4 hrs | >1 <2 hrs. | <1 hr. |

SWAI = Slatwall aluminum insert
GBMS = Grit blasted mild steel

Example 2

An investigation was performed to evaluate certain substituted-urea hydrogen peroxide complexes as potential replacements for the alkyl hydroperoxides in anaerobic curable compositions.

The compounds of Table 3 were mixed together by hand in a plastic bottle to form a base acrylate composition. The resulting base acrylate composition was then sonicated for 1 hour to dissolve the saccharin.

TABLE 3

| Compound | Amount (phr) |
| --- | --- |
| Poly(ethylene glycol) methacrylate | 100 |
| Radical inhibitor solution | 0.23 |
| Chelator solution | 0.96 |
| Saccharin | 1.73 |
| N,N-diethyl-p-toluidine | 0.61 |
| N,N-dimethyl-o-toluidine | 0.30 |

A complex of N,N' dimethyl urea and hydrogen peroxide ("dimethyl UHP") and a complex of tetramethyl urea and hydrogen peroxide ("tetramethyl UHP") were prepared according to the synthesis scheme of FIG. 3.

Individual sample compositions were prepared according to the formulations of Table 4. Each sample composition contained an equal amount of the base acrylate composition of Table 3 and a different peroxide-based initiator. The samples were prepared by hand mixing the components in individual 30 ml bottles. The formulation with the complex of urea and hydrogen peroxide ("UHP"), Composition 2-2, was sonicated for 45 minutes after mixing in order to dissolve the UHP which is initially in solid form. It was observed that dimethyl UHP and tetramethyl UHP had significantly improved solubility in non-polar acrylic monomers compared with UHP.

TABLE 4

|  | Composition 2-1 | Composition 2-2 | Composition 2-3 | Composition 2-4 |
| --- | --- | --- | --- | --- |
| Base (from Table 3) | 10 g | 10 g | 10 g | 10 g |
| CHP | 0.10 g | — | — | — |
| UHP | — | 0.057 g | — | — |
| Dimethyl UHP | — | — | 0.073 g | — |
| Tetramethyl UHP | — | — | — | 0.09 g |

CHP = cumene hydroperoxide
UHP = urea hydrogen peroxide complex
Dimethyl UHP = complex of N, N' dimethylurea and hydrogen peroxide
Tetramethyl UHP = complex of tetramethylurea and hydrogen peroxide Breakloose adhesion testing was performed according to ASTM D5649. Breakloose torque is the initial torque required to decrease or eliminate the axial load in a seated assembly. Twenty nut and bolt specimens were assembled for each adhesive formulation tested. Adhesive was applied to the bolt, and the nut was screwed onto the bolt with a steel collar as a spacer. For the break adhesion tests, the specimens were maintained at ambient temperature for 15 minutes, 30 minutes, 1 hour and 24 hours after assembly (five specimens each). The break strengths (in-lb$_f$) were then recorded for five specimens of each adhesive formulation after 15 minutes, 30 minutes, 1 hour and after 24 hours at ambient temperature (25° C.) and 45-50% relative humidity, respectively. The data for these evaluations is set forth below in Table 5.

As can be seen in Table 5, the tested nut/bolt specimens to which were added an amount of Compositions 2-2, 2-3, and 2-4, containing UHP, dimethyl UHP, and tetramethyl UHP, respectively, exhibited surprisingly comparable break strengths when compared with those break strength values of Compositions 2-1 which contained the conventional peroxide-based curative agent cumene hydroperoxide. It was also observed that Compositions 2-2, 2-3, and 2-4 did not give off the objectionable odor commonly associated with alkyl hydroperoxides like CHP.

TABLE 5

| Time Interval | Composition 2-1 | Composition 2-2 | Composition 2-3 | Composition 2-4 |
|---|---|---|---|---|
| 15 minutes | 14 in. lbs.* | 0 in. lbs. | 0 in. lbs. | 0 in. lbs. |
| 30 minutes | 130 ± 21 in. lbs. | 5 ± 2 in. lbs. | 8 in. lbs.* | 47 in. lbs.* |
| 60 minutes | 195 ± 32 in. lbs. | 86 in. lbs.* | 101 in. lbs.* | 220 in. lbs.* |
| 240 minutes | 254 ± 31 in. lbs. | 280 ± 29 in. lbs. | 263 ± 40 in. lbs. | 260 ± 58 in. lbs. |
| 1440 minutes | 262 ± 29 in. lbs. | 295 ± 11 in. lbs. | 292 ± 18 in. lbs. | 292 ± 18 in. lbs. |

*test result values were too scattered for a meaningful standard deviation calculation.

Example 3

An investigation was performed to evaluate a complex of N-methylpyrrolidinone and hydrogen peroxide as a potential replacement for the alkyl hydroperoxide curatives in anaerobic curable compositions.

The compounds of Table 6 were mixed together by hand in a plastic dropper bottle to form a base acrylate composition.

TABLE 6

| Compound | Amount (phr) |
|---|---|
| Poly(ethyleneglycol) methacrylate | 100 |
| Radical inhibitor solution | 0.23 |
| Chelator solution | 0.96 |
| Saccharin | 1.73 |
| APH | 0.25 |
| Maleic Acid | 0.50 |

Figure 2:
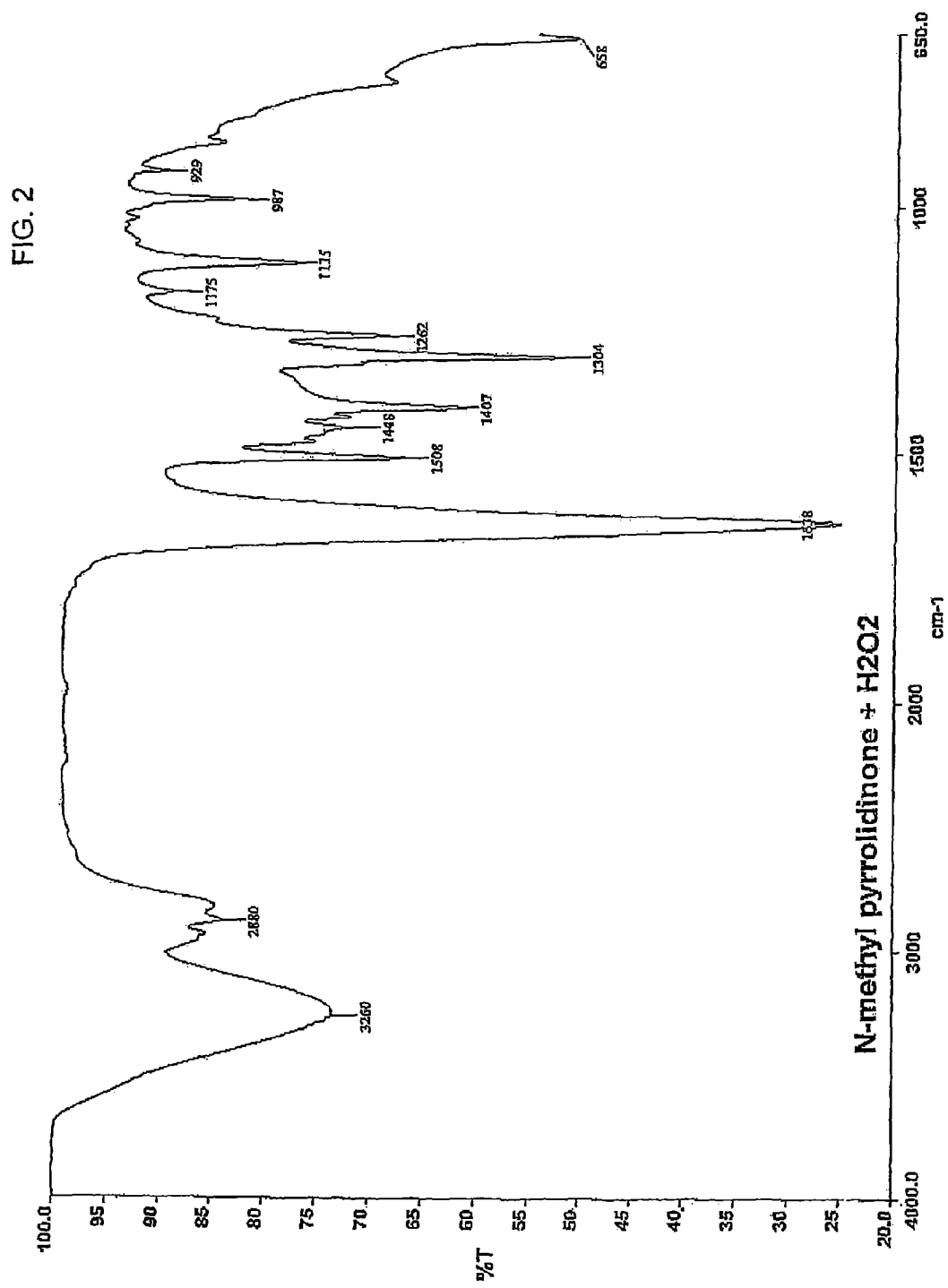
FIG. 2 depicts an IR spectrum of a N-methyl pyrrolidinone+H₂O₂ complex of Example 3 according to the present invention.

A complex of N-methylpyrrolidinone and $H_2O_2$ was formulated as follows. 9.9 g (100 mmol) of N-methylpyrrolidinone ("NMP") and 8.75 g of 50% aq. hydrogen peroxide (125 mmol) were combined in a 50 mL Erlenmeyer flask. The solution was heated on a stirrer/hot plate to approximately 60° C. After stirring at 60° C., the solution was poured into a 125 mL crystallization dish, and water was allowed to evaporate for 72 hours at ambient temperature. This process yielded 14.7 g of NMP/$H_2O_2$ complex. The complex was analyzed by $^1$H NMR (shown in FIG. 1) and FT-IR (shown in FIG. 2). The complex was essentially odorless.

Individual sample compositions were prepared according to the formulations of Table 7. Each sample composition contained an equal amount of the base acrylate composition of Table 6 and a different peroxide-based curative agent. The samples were prepared by hand mixing the components in small plastic dropper bottles.

TABLE 7

| | Composition 3-1 | Composition 3-2 | Composition 3-3 | Composition 3-4 |
|---|---|---|---|---|
| Base (from Table 6) | 10 g | 10 g | 10 g | 10 g |
| CHP | 0.10 g | 0.3 g | — | — |
| NMP/$H_2O_2$ | — | — | 0.09 g | 0.27 g |

CHP = cumene hydroperoxide
NMP/$H_2O_2$ = complex of N-methyl pyrridinone and hydrogen peroxide The compositions were aged at ambient temperature for 2 days. Breakloose adhesion testing was performed according to ASTM D5649 in a manner as discussed above. The break and prevail torque strengths (in-lb$_f$) were recorded for five specimens of each adhesive composition after 15 minutes, 30 minutes, 1 hour and after 24 hours at ambient temperature (25° C.) and 45-50% relative humidity, respectively. The data for these evaluations is set forth below in Table 8.

As can be seen in Table 8, the tested nut/bolt specimens to which were added an amount of Compositions 3-3 and 3-4, containing a NMP/$H_2O_2$ complex exhibited surprisingly comparable break strengths when compared with those break strength values of Compositions 3-1 and 3-2 which contained the conventional peroxide-based curative agent cumene hydroperoxide.

TABLE 8

| Time Interval | Composition 3-1 | Composition 3-2 | Composition 3-3 | Composition 3-4 |
| --- | --- | --- | --- | --- |
| 15 minutes | 132 ± 23 in. lbs. | 125 ± 29 in. lbs. | 17 ± 7 in. lbs. | 21 ± 8 in. lbs. |
| 30 minutes | 177 ± 33 in. lbs. | 160 ± 30 in. lbs. | 80 ± 11 in. lbs. | 105 ± 22 in. lbs. |
| 60 minutes | 211 ± 28 in. lbs. | 158 ± 23 in. lbs. | 154 ± 33 in. lbs. | 207 ± 10 in. lbs. |
| 240 minutes | 251 ± 37 in. lbs. | 143 ± 40 in. lbs. | 271 ± 16 in. lbs. | 232 ± 26 in. lbs. |
| 1440 minutes | 251 ± 32 in. lbs. | 150 ± 29 in. lbs. | 234 ± 40 in. lbs. | 282 ± 33 in. lbs. |

Example 4

An investigation was performed to evaluate a complex of N-dodecyl pyrrolidinone and hydrogen peroxide as a potential replacement for the alkyl hydroperoxide curatives in anaerobic curable compositions.

The compounds of Table 9 were mixed together by hand in a plastic dropper bottle to form a base acrylate composition. The resulting base acrylate composition was then sonicated for 2 hours to dissolve the solid components.

TABLE 9

| Compound | Amount (phr) |
| --- | --- |
| Poly(ethyleneglycol) methacrylate | 100 |
| Radical inhibitor solution | 0.23 |
| Chelator solution | 0.96 |
| Saccharin | 1.73 |
| APH | 0.25 |
| Maleic Acid | 0.50 |

A complex of N-dodecyl pyrrolidinone and hydrogen peroxide was prepared as follows. 12.7 g (50 mmol) of N-dodecyl pyrrolidinone and 6.8 g of 50% aq. hydrogen peroxide (100 mmol) were combined in a 50 mL Erlenmeyer flask. The solution was heated on a stirrer/hot plate to approximately 60° C. with stirring. The reaction mixture remained cloudy during the heating. After stirring at 60° C. for 5 minutes, the solution was poured into a crystallization dish. Two phases were apparent. The water was allowed to evaporate for 72 hours at ambient temperature. This process yielded 15.3 g of N-dodecyl pyrrolidinone/$H_2O_2$ complex. The complex was essentially odorless.

Individual sample compositions were prepared according to the formulations of Table 10. Each sample composition contained an equal amount of the base acrylate composition of Table 9 and a different peroxide-based curative agent. The samples were prepared by hand mixing the components in small plastic dropper bottles.

TABLE 10

| | Composition 4-1 | Composition 4-2 | Composition 4-3 | Composition 4-4 |
| --- | --- | --- | --- | --- |
| Base (from Table 9) | 10 g | 10 g | 10 g | 10 g |
| CHP | 0.10 g | 0.3 g | — | — |
| Dodecyl Pyrr/$H_2O_2$ | — | — | 0.19 g | 0.57 g |

CHP = cumene hydroperoxide
Dodecyl Pyrr/$H_2O_2$ = complex of dodecyl pyrrolidinone and hydrogen peroxide Breakloose adhesion testing was performed according to ASTM D5649 in a manner as discussed above. The break and prevail torque strengths (in-$lb_f$) were recorded for five specimens of each adhesive composition after 15 minutes, 30 minutes, 1 hour and after 24 hours at ambient temperature (25° C.) and 45-50% relative humidity, respectively. The data for these evaluations is set forth below in Table 11.

TABLE 11

| Time Interval | Composition 4-1 | Composition 4-2 | Composition 4-3 | Composition 4-4 |
| --- | --- | --- | --- | --- |
| 15 minutes | 3 in. lbs.* | 6 in. lbs.* | 23 in. lbs.* | 11 in. lbs.* |
| 30 minutes | 52 ± 27 in. lbs. | 54 ± 27 in. lbs. | 28 in. lbs.* | 19 in. lbs.* |
| 60 minutes | 152 ± 55 in. lbs. | 146 ± 38 in. lbs. | 101 in. lbs.* | 26 in. lbs.* |
| 240 minutes | 239 ± 40 in. lbs. | 188 ± 33 in. lbs. | 36 in. lbs.* | 20 in. lbs.* |
| 1440 minutes | 260 ± 35 in. lbs. | 268 ± 38 in. lbs. | 73 in. lbs.* | 21 ± 2 in. lbs. |

*test result values were too scattered for a meaningful standard deviation calculation.

Example 5

An investigation was performed to evaluate a complex of N-diacetone acrylamide and hydrogen peroxide as a potential replacement for the alkyl hydroperoxide curatives in anaerobic curable compositions.

A complex of N-diacetone acrylamide and hydrogen peroxide was synthesized and this complex was found to have significantly improved solubility over a complex of urea and hydrogen peroxide ("UHP," as discussed above) in non-polar acrylic monomers. The N-diacetone acrylamide/$H_2O_2$ complex was essentially odorless.

The N-diacetone acrylamide/$H_2O_2$ complex was used as the peroxide curative in a model anaerobic threadlocking adhesive and it was found to work as well as cumene hydroperoxide, the standard hydroperoxide in anaerobic adhesives. It is believed this concept would also work with N,N-dialkyl acrylamides.

We claimed:

1. An anaerobic cure system comprising:
(a) a complex comprising (1) hydrogen peroxide and (ii) at least one compound represented by Formula I:

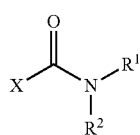
(I)

wherein X is selected from the group consisting of

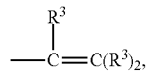

—C(R³)₃, —C≡C(R³), —O(R³), —N(R³)₂, and —S(R³); and

R¹, R², and R³ are each independently selected from the group consisting of H, alkyl, alkenyl, alkynyl, aralkyl, aryl, heteroaryl, heteroarylalkyl, heterocyclyl, and cycloalkyl, or R² and an R³ are optionally taken together to form an alicyclic ring, provided that when X is —N(R³)₂ and Formula I is represented by the structure:

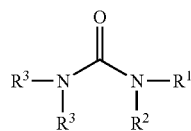

at least one of R¹, R², and at least one of R³, are each independently selected from alkyl groups; and (b) one or more anaerobic cure components selected from the group consisting of saccharin, toluidines and acetyl phenyl hydrazine.

2. The anaerobic cure system of claim 1, wherein hydrogen peroxide is present in an amount ranging from 0.33 to about 2.0 equivalents based on the total equivalents of the complex.

3. The anaerobic cure system of claim 1, wherein R¹ and at least one R³ are independently selected from C₁-C₃ alkyl groups.

4. A method of preparing an anaerobic curable composition, comprising mixing a meth(acrylate) component and the anaerobic cure system of claim 1.

5. An anaerobic cure system comprising:
(a) a complex comprising (i) hydrogen peroxide and (ii) at least one compound represented by Formula I:

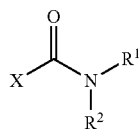
(I)

wherein X is selected from the group consisting of

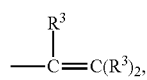

—C(R³), —C≡C(R³), —O(R³), and —S(R³); and R¹, R², and R³ are each independently selected from the group consisting of H, alkyl, alkenyl, alkynyl, aralkyl, aryl, heteroaryl, heteroarylalkyl, heterocyclyl, and cycloalkyl, or R² and an R³ are optionally taken together to form an alicyclic ring; and (b) one or more anaerobic cure components selected from the group consisting of saccharin, toluidines and acetyl phenyl hydrazine, provided that when X is

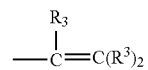

and Formula I is represented by the structure:

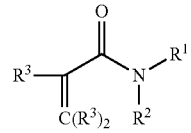

at least one of R¹ or R², and at least one R³ is each independently selected from alkyl groups.

6. The anaerobic cure system of claim 5, wherein R¹, R², and R³ are each independently, selected from hydrogen and alkyl groups.

7. An anaerobic cure system comprising:
(a) a complex comprising (i) hydrogen peroxide and (ii) at least one compound represented by Formula I:

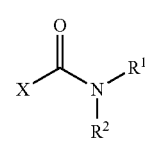
(I)

wherein X is selected from the group consisting of

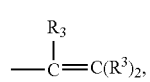

—C(R³)₃, —C≡C(R³), —O(R³), and —S(R³); and R¹, R², and R³ are each independently selected from the group consisting of H, alkyl, alkenyl, alkynyl, aralkyl, aryl, heretoaryl heteroarylalkyl, heterocyclyl, and cycloalkyl, or R² and an R³ are optionally taken together to form an alicyclic ring; and (b) one or more anaerobic cure components selected from the group consisting of saccharin, toluidines and acetyl phenyl hydrazine, provided that when X is —C(R³)₃ at least one of R¹ or R², and at least one R³ is each independently selected from alkyl groups.

8. An anaerobic cure system comprising:
(a) a complex comprising (i) hydrogen peroxide and (ii) at least one compound represented by Formula I:

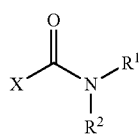

(I)

wherein X is selected from the group consisting of

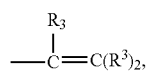

—C(R$^3$)$_3$, —C≡C(R$^3$), —O(R$^3$), and —S(R$^3$); and R$^1$, R$^2$, and R$^3$ are each independently selected from the group consisting of H, alkyl, alkenyl, alkynyl, aralkyl, aryl, heteroaryl heteroarylalkyl, heterocyclyl, and cycloalkyl, or R$^2$ and an R$^3$ are optionally taken together to form an alicyclic ring; and
(b) one or more anaerobic cure components selected from the group consisting of saccharin, toluidines and acetyl phenyl hydrazine, provided that when X is —C(R$^3$)$_3$ at least one of R$^1$ or R$^2$, and at least one of R$^3$ is each independently selected from alkyl groups, wherein R$^3$ and R$^2$ are taken together to form a C$_2$-C$_6$ alicyclic ring, and Formula I is represented by the following structure:

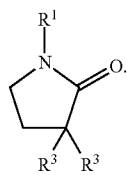

9. The anaerobic cure system of claim 8, wherein R$^1$ is selected from H and alkyl.

10. The anaerobic cure system of claim 8, wherein R$^1$ is a C$_1$-C$_{12}$ alkyl group.

11. An anaerobic cure system, comprising
a complex hydrogen peroxide and at least one compound selected from the group consisting of: N-substituted urea, N-substituted pyrrolidinone, and N-substituted acrylamide; and one or more anaerobic cure components selected from the group consisting of accelerators, stabilizers, and reducing agents.

12. An anaerobic curable composition, comprising
a (meth)acrylate component; and
an anaerobic system according to claim 11; and
one or more anaerobic cure components selected from the group consisting of accelerators, stabilizers, and reducing agents.

13. The composition of claim 12, wherein the total amount of the one or more anaerobic cure components is between about 1 and about 10 wt % based on the total weight of the composition.

14. The composition of claim 12, wherein the (meth)acrylate component comprises compounds represented by H$_2$C═CGCO$_2$R$^4$, wherein G is a member selected from the group consisting of hydrogen, halogen and alkyl having from 1 to about four carbon atoms, and R$^4$ is a member selected from the group consisting of alkyl, cycloalkyl, alkenyl, cycloalkenyl, alkaryl, and aryl groups having from 1 to about 16 carbon atoms, with or without substitution or interruption by a member selected from the group consisting of silane, silicon, oxygen, halogen, carbonyl, hydroxyl, ester, carboxylic acid, urea, urethane, carbamate, amine, amide, sulfur, sulonate, and sulfone.

15. The composition of claim 12, wherein the (meth)acrylate component comprises members selected from the group consisting of silicone (meth)acrylates, polyethylene glycol di(meth)acrylates, bisphenol-A-(meth)acrylates, ethoxylated bisphenol-A-(meth)acrylates, bisphenol-F-(meth)acrylates, ethoxylate bisphenol-F-(meth)acrylates, tetrahydrofuran (meth)acrylates and di(meth)acrylates, hydroxypropyl (meth)acrylate, hexanediol di(meth)acrylate, and trimethylol propane tri(meth)acrylate.

16. The composition of claim 12, wherein the complex is present in an amount of between about 0.1 and 10 wt % based on the total weight of the composition.

17. An article prepared from the composition of claim 12.

18. A method of bonding together two or more substrates, comprising:
(a) providing at least two substrates;
(b) dispensing onto a surface of one or both of the at least two substrates an anaerobic adhesive composition of claim 12;
(c) contacting the surface of the at least two substrates having the anaerobic adhesive composition thereon; and
(d) exposing the adhesive composition to anaerobic conditions sufficient to effect cure.

19. A method of bonding together two or more substrates, comprising:
(a) providing at least two substrates;
(b) dispensing onto a surface of one or both of the at least two substrates a primer composition;
(c) dispensing onto the substrate onto which the primer has been dispensed an anaerobic adhesive composition of claim 12;
(d) contacting the surfaces of the at least two substrates having the anaerobic adhesive composition thereon; and
(e) exposing the adhesive composition to anaerobic conditions sufficient to effect cure.

* * * * *

UNITED STATES PATENT AND TRADEMARK OFFICE
CERTIFICATE OF CORRECTION

PATENT NO. : 8,524,034 B2
APPLICATION NO. : 13/177921
DATED : September 3, 2013
INVENTOR(S) : Philip T. Klemarczyk et al.

It is certified that error appears in the above-identified patent and that said Letters Patent is hereby corrected as shown below:

On the Title Page

In item [57], Abstract: After "heteroaryl", insert -- , --.

In the Specification

Column 1, Line 39: Change "diperphithalate" to -- diperphthalate --.

Column 2, Line 20: After "heteroaryl", insert -- , --.

Column 2, Line 47: After "heteroaryl", insert -- , --.

Column 3, Line 10: After "heteroaryl", insert -- , --.

Column 3, Line 38: After "heteroaryl", insert -- , --.

Column 6, Line 19: After "heteroaryl", insert -- , --.

Column 8, Line 40: After "heteroaryl", insert -- , --.

Column 9, Line 11: After "eroaryl", insert -- , --.

Column 9, Line 38: After "heteroaryl", insert -- , --.

Column 13, Line 54: Change "orheterocyclic", to -- or heterocyclic --.

Signed and Sealed this
Twenty-seventh Day of June, 2017

Joseph Matal
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 8,524,034 B2

In the Claims

Column 24, Line 57: Change "heretoaryl" to -- heteroaryl, --.

Column 25, Line 18: After "heteroaryl", insert -- , --.

Column 26, Line 16: Change "sulonate" to -- sulfonate --.